(12) United States Patent
Coello et al.

(10) Patent No.: US 6,358,473 B1
(45) Date of Patent: Mar. 19, 2002

(54) MICROSCOPE SLIDE HEATER

(76) Inventors: Albert Coello, 535 Walten Way, Windsor, CA (US) 95492; John Johnson, 7808 Medallion Way, Rohnert Park, CA (US) 94928; David Tacha, 613 Guayas Ct., San Ramon, CA (US) 94586

( * ) Notice: Subject to any disclaimer, the term of this patent is extended or adjusted under 35 U.S.C. 154(b) by 0 days.

(21) Appl. No.: 09/412,180

(22) Filed: Oct. 5, 1999

(51) Int. Cl.$^7$ ................................................. B01L 9/00
(52) U.S. Cl. ..................... 422/99; 422/297; 422/300; 435/303.1; 359/395; 219/385; 219/521
(58) Field of Search ................... 118/59, 500, 501, 118/503; 427/2.11, 2.13, 372.2; 422/58, 62, 99, 297, 300; 435/303.1; 359/395; 219/385, 521; 236/3; 237/3

(56) References Cited

U.S. PATENT DOCUMENTS

| | | | |
|---|---|---|---|
| 4,043,292 A | 8/1977 | Rogers et al. | 118/642 |
| 4,384,193 A | * 5/1983 | Kledzik et al. | 219/521 |
| 4,413,584 A | 11/1983 | DiMaggio, Jr. et al. | 118/56 |
| 4,651,671 A | 3/1987 | Pedersen | 118/57 |
| 4,738,824 A | 4/1988 | Takeuchi | 422/63 |
| 5,061,630 A | * 10/1991 | Knopf et al. | 435/286.1 |
| 5,439,649 A | * 8/1995 | Tsung et al. | 422/99 |
| 5,700,346 A | 12/1997 | Edwards | 156/357 |
| RE35,716 E | * 1/1998 | Stapleton et al. | 435/3 |

OTHER PUBLICATIONS

Fisher Catalog—Hotplates—pp. 610–617, 1988.*

* cited by examiner

*Primary Examiner*—Laura Edwards
(74) *Attorney, Agent, or Firm*—Jack Lo

(57) ABSTRACT

A microscope slide stainer includes a waste bin with an open top, and supporting notches arranged on the top edges of opposite sides. A slide supporting rack is supported in a horizontal position across the top of the bin in the supporting notches. The rack includes a pair of rails extending along a horizontal base. Brackets arranged on top of the rails define a plurality of spaced-apart slide holding positions. A hot plate is positioned between the rails and spaced above the horizontal base. A control box is attached to the hot plate for temperature control. Pins extending from opposite sides of the hot plate ride in direction-changing slots in the rails to enable the hot plate to be moved between a raised position engaged against the bottom of the slides, and a lowered position disengaged from the slides. Grooves are arranged on top surface of the hot plate to prevent the wet slides from sticking to it. A cover is removably positioned over the rack to define a heating and humidity chamber. The rack can be placed in a tilted position for rinsing the slides by inserting its ends in slanted slots extending downwardly from the supporting notches on the bin.

26 Claims, 6 Drawing Sheets

MICROSCOPE SLIDE HEATER

BACKGROUND OF THE INVENTION

1. Field of the Invention

This invention relates generally to microscope slide stainers.

2. Prior Art

Many types of biological specimens for microscopic examination are stained with color to increase contrast for better viewing. The process includes placing the specimen on a transparent microscope slide, applying a staining solution or reagent to the specimen, heating the specimen to a suitable temperature, and rinsing off the reagent. The staining process is very time consuming when done with separate equipment. Cross contamination between the slides occurs when they are transferred by hand from one piece of equipment to another, and also when the slides are stained by being submerged in the same reagent container.

Many mechanized slide stainers have been disclosed for automating the process. A stainer disclosed in U.S. Pat. No. 5,770,346 to Edwards includes a conveyer for automatically taking slides stored around a carousel and transporting them across several staining stations, including a heating station, and finally dropping them into a slide collection bin. A stainer disclosed in U.S. Pat. No. 4,738,824 to Takeuchi includes a robotic arm for dipping racks of slides in a plurality of baths. However, cross contamination occurs because the slides are submerged in the same baths. A stainer disclosed in U.S. Pat. No. 4,651,671 to Pedersen includes a plurality of pivoted robotic arms attached to a conveyer for dipping individual slides in a plurality of baths. Cross contamination also occurs because the slides are submerged in the same baths. A stainer disclosed in U.S. Pat. No. 4,413,584 to DiMaggio, Jr. et al. includes pivotable slide trays for tilting up the slides to assist runoff during rinsing. However, no heater is included. A stainer disclosed in U.S. Pat. No. 4,043,292 to Rogers et al. includes a carousel with radial arms for carrying slides to staining and heating stations. The arms are pivotable for tilting the slides. The slides are heated by being positioned on a heated platen. However, the wet slides will stick to the smooth top surface of the heated platen, so that they will be difficult to remove.

All fully automated slide stainers are complicated, and thus very expensive. They use large quantities of very expensive reagents. Many have transparent covers that allow radiated heat loss, which lengthens the warm up time. Many hold slides vertically, so that the slides cannot be observed during the staining process. Although some hold slides horizontally, they have darker or cluttered backgrounds that reduce contrast and hinder slide observation.

OBJECTS OF THE INVENTION

Accordingly, objects of the present microscope slide stainer are:

to stain-microscope slides;
to reduce human handling of the slides;
to heat the slides to selectable temperatures;
to start and stop heating very quickly;
to enable the slides to be seen clearly;
to prevent the slides from drying out;
to prevent the wet slides from sticking;
to tilt the slides to assist runoff during rinsing;
to prevent the runoff from each slide from crossing over onto adjacent slides; and
to prevent radiated heat loss for significantly faster warm up.

Further objects of the present invention will become apparent from a consideration of the drawings and ensuing description.

BRIEF SUMMARY OF THE INVENTION

A microscope slide stainer includes a waste bin with an open top, and supporting notches arranged on the top edges of opposite sides. A slide supporting rack is supported in a horizontal position across the top of the bin in the supporting notches. The rack includes a pair of rails extending along a horizontal base. Brackets arranged on top of the rails define a plurality of spaced-apart slide holding positions. A hot plate is positioned between the rails and spaced above the horizontal base. A control box is attached to the hot plate for temperature control. Pins extending from opposite sides of the hot plate ride in direction-changing slots in the rails to enable the hot plate to be moved between a raised position engaged against the bottom of the slides, and a lowered position disengaged from the slides. Grooves are arranged on top surface of the hot plate to prevent the wet slides from sticking to it. A cover is removably positioned over the rack to define a heating and humidity chamber. The rack can be placed in a tilted position for rinsing the slides by inserting its ends in slanted slots extending downwardly from the supporting notches on the bin.

Figure 1:
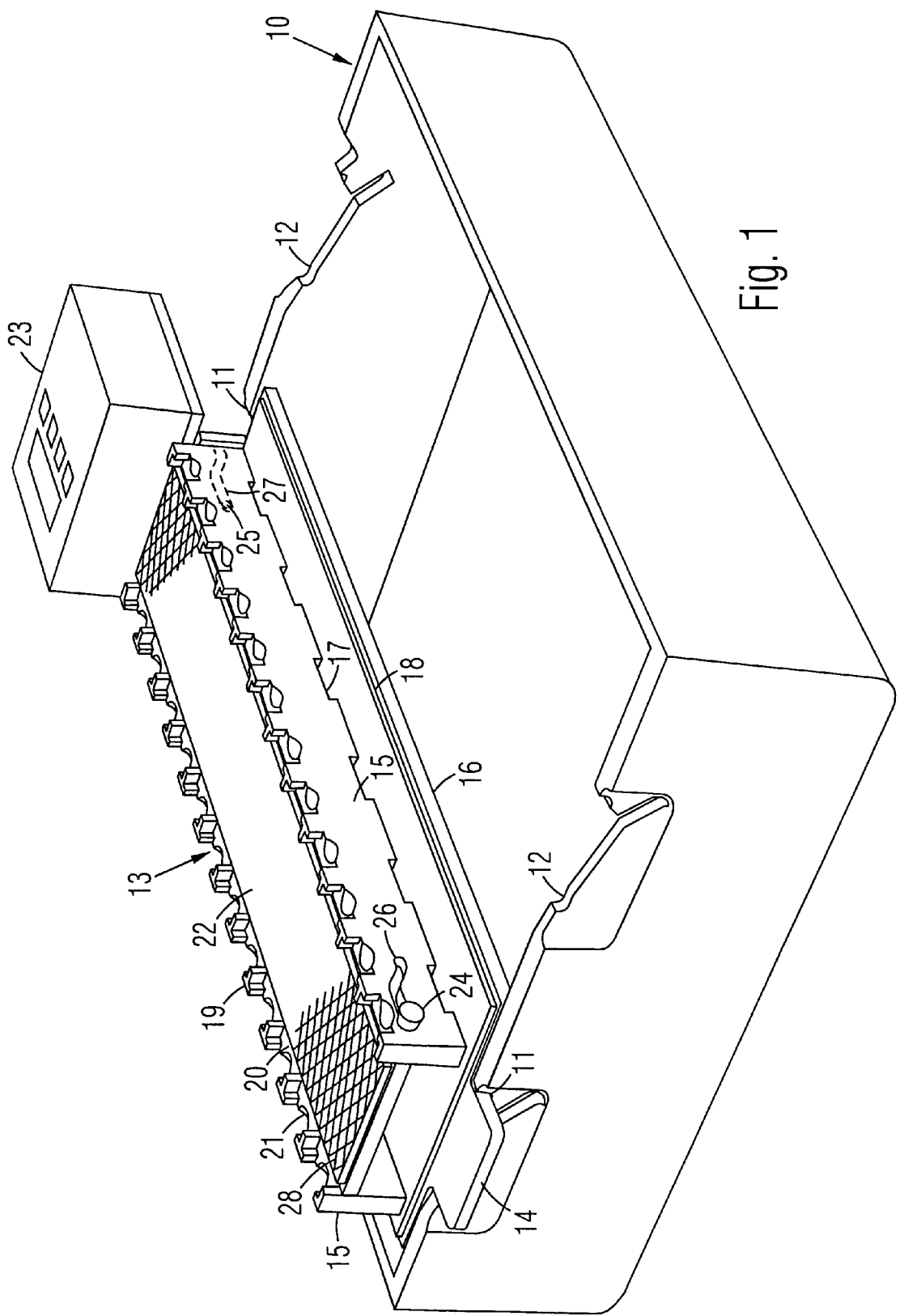
FIG. 1 is a side perspective view of the present microscope slide stainer with one slide supporting rack in position.

| DRAWING REFERENCE NUMERALS | |
|---|---|
| 10. Bin | 11. Supporting Notches |
| 12. Supporting Notches | 13. Slide Supporting Rack |
| 14. Tabs | 15. Rails |
| 16. Horizontal Base | 17. Drainage slots |
| 18. Shoulder | 19. Brackets |
| 20. Slide Holding Positions | 21. Finger Notches |
| 22. Hot Plate | 23. Control Box |
| 24. Pins | 25. Pins |
| 26. Direction-Changing Slot | 27. Direction-Changing Slot |
| 28. Grooves | 29. Slides |
| 30. Hydrophobic Barriers | 31. Specimen |
| 32. Covers | 33. Slanted Supporting Slots |
| 34. Heating Element | |

DETAILED DESCRIPTION OF THE INVENTION

FIG. 1:

A preferred embodiment of the microscope slide stainer is shown in FIG. 1. It includes a waste collection bin 10 with an open top, and two pairs of supporting notches 11 and 12 arranged on opposite rims. A slide supporting rack 13 is supported in a horizontal position across the top of bin 10 by tabs 14 (one shown) at the ends of rack 13 positioned in notches 11. Rack 13 includes a pair of rails 15 extending along a horizontal base 16. Drainage slots 17 are arranged at the base of one of rails 15. A shoulder 18 is arranged around the perimeter on top of base 16. Brackets 19 arranged on top of rails 15 define a plurality of spaced-apart slide holding positions 20. Finger notches 21 are arranged at opposite ends of slide holding positions 20 between brackets 19. Much of rack 13 is preferably made of "CORIAN" by Dow Coming for resistance to acids, bases, stains, and heat.

An electrically activated, elongated hot plate 22 is movably positioned between rails 15 and spaced above horizontal base 16. Hot plate 22 is covered by a conventional heat resistant powder-coat white paint which is resistant to heat, stains, and chemicals. A control box 23 housing conventional electronics is connected to hot plate 22 for precise temperature control. Two pair of pins 24 and 25 (one of each pair shown) extending from opposite longitudinal edges of hot plate 22 respectively ride in direction-changing slots 26 and 27 in rails 15 to enable hot plate 22 to be moved between raised and lowered positions. Slots 26 and 27 each preferably include upper and lower horizontal sections connected by a slanted section. Slots 26 extend completely through rails 15, so that removable thumb-screw pins 24 extend through them. Slots 27 are preferably arranged only on the interior sides of rails 15, so that pins 25 do not extend through rails 15. The outer ends of slots 27 extend to the ends of rails 15, so that when thumb-screw pins 24 are unscrewed, hot plate 22 can be completely detached from rails 15 by sliding pins 25 out of slots 27. Grooves 28 are arranged on the top surface of hot plate 22 to provide air channels that prevent wet slides from sticking to it, and also to provide drainage for preventing liquid on the slides from flowing onto adjacent slides. Grooves 28 are preferably arranged in a diamond-shaped pattern.

Figure 2:
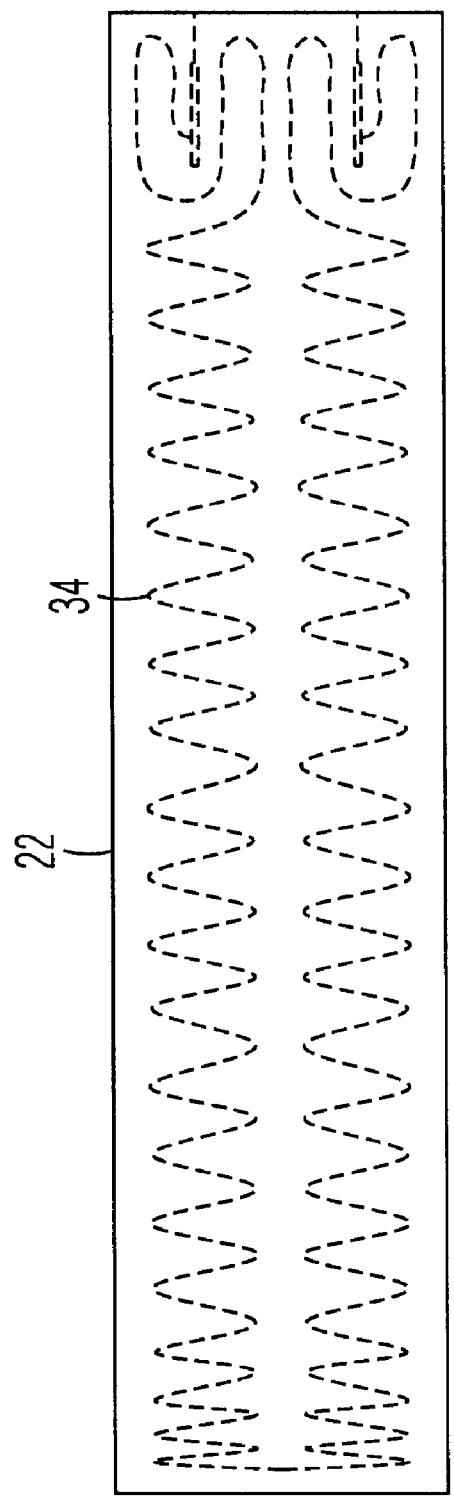
FIG. 2 is a top view of a hot plate of the slide stainer.

FIG. 2:

A heating element 34 is embedded within hot plate 22 in FIG. 2. Heating element 34 is arranged in a zigzag pattern which is denser at the ends of hot plate 22 for providing even heating across the entire length of hot plate 22.

Figure 3:
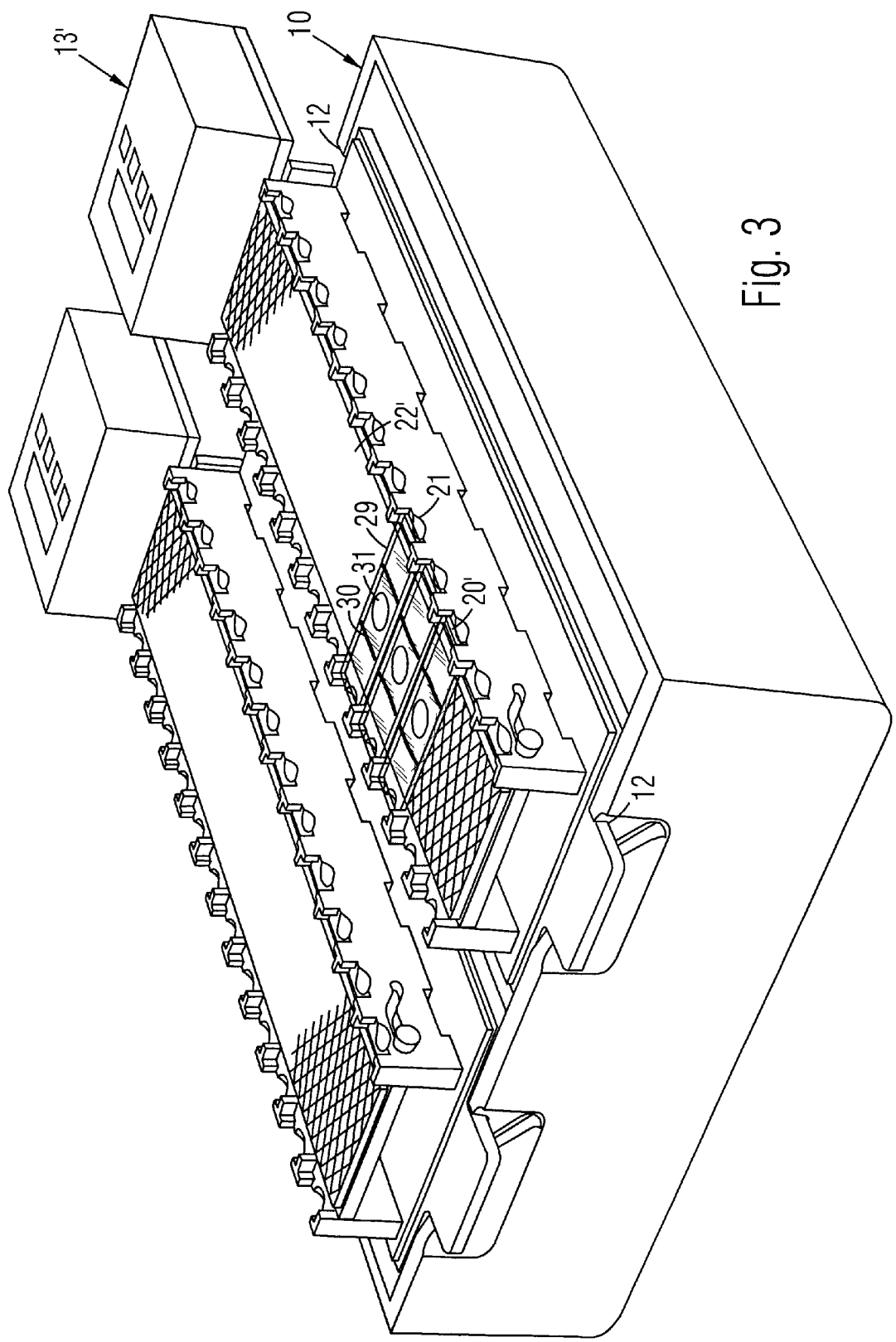
FIG. 3 is a side perspective view of the microscope slide stainer with both slide supporting racks in position and hot bars in a raised position.

FIG. 3:

An additional slide supporting rack 13' is positioned in a horizontal position in supporting notches 12 on bin 10 in FIG. 3. Several microscope slides 29 are placed in slide holding positions 20'. Finger notches 21 enable the ends of slides 29 to be easily gripped for removal. A pair of hydrophobic or liquid barriers 30 are drawn, preferably with a hydrophobic pen, across each slide 29 around specimens 31. A reagent is applied to slides 29 between the hydrophobic barriers. Barriers 30 limit the area that the reagent can cover on each slide so as to significantly reduce reagent usage. Because the reagent is applied to slides 29 individually, it is prevented from crossing between spaced apart slides 29, so that cross contamination during reagent application is eliminated. Hot plate 22' is in the raised position engaged against the bottom of slides 29, and can be operated to heat slides 29 to a selected temperature. Since most of rack 13' is made of a heat insulating material, it can be handled comfortably even while hot plate 22' is in operation. Hot plate 22' is preferably white in color for providing a light homogeneous background that facilitates viewing stained tissues on the slides. Hot plate 22' is particularly useful for applications such as digestion, drying liquid mounting media, denaturing procedures for in situ hybridization, and isothermic temperature control.

Figure 4:
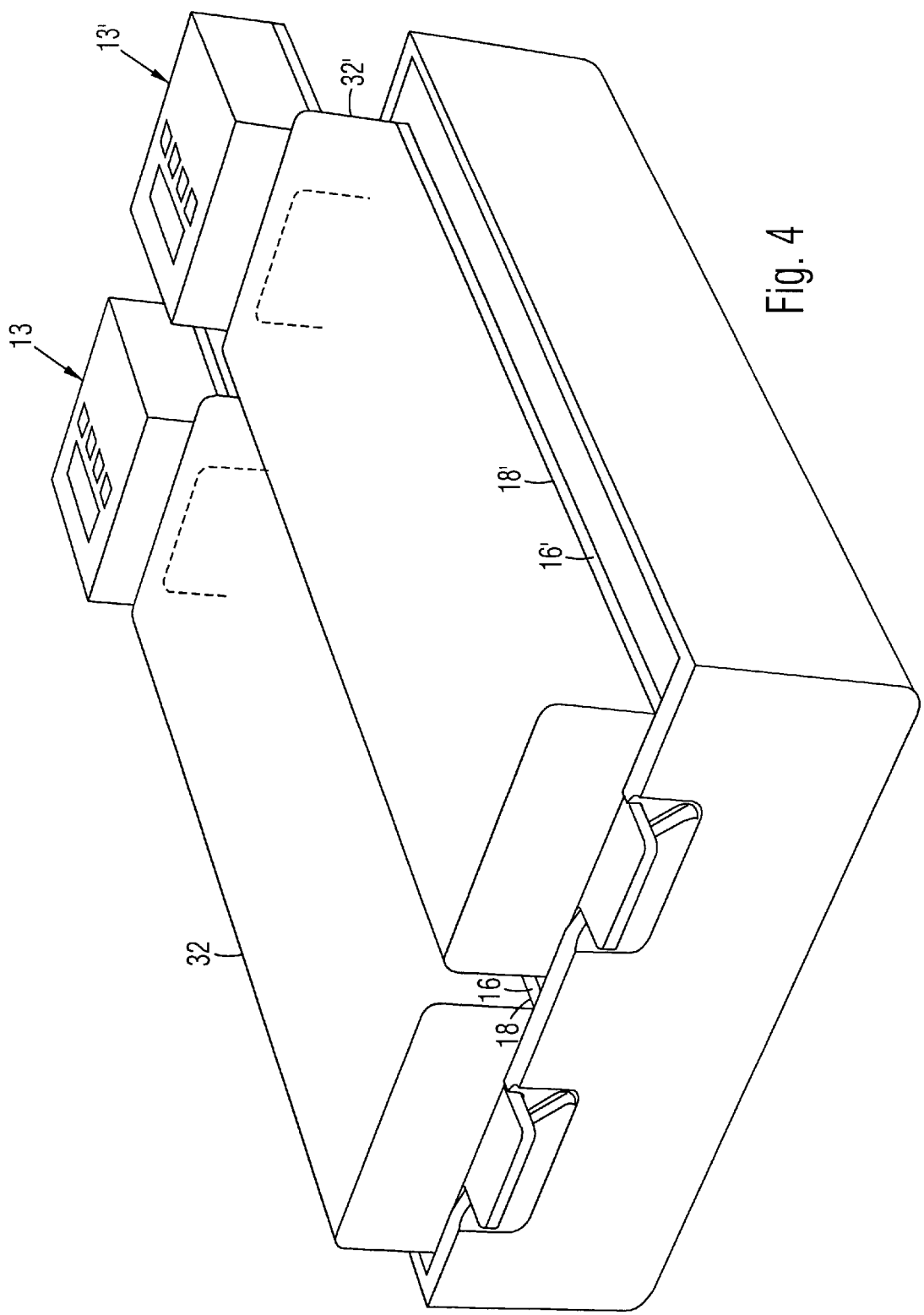
FIG. 4 is a side perspective view of the microscope slide stainer with the slide supporting racks covered.

FIG. 4:

As shown in FIG. 4, a pair of covers 32 and 32' are removably positioned on shoulders 18 and 18' of bases 16 and 16' of slide supporting rack 13 and 13' to define heating and humidity chambers that prevent the slides from drying out. Covers 32 and 32' may be opaque for preventing radiant heat loss, and thus significantly speeding up the warm up time. Alternatively, covers 32 and 32' may be transparent for viewing the slides. The hot plates (not shown) can be completely removed before applying covers 32 and 32' so that the stainer is used only as humidity chambers.

Figure 5:
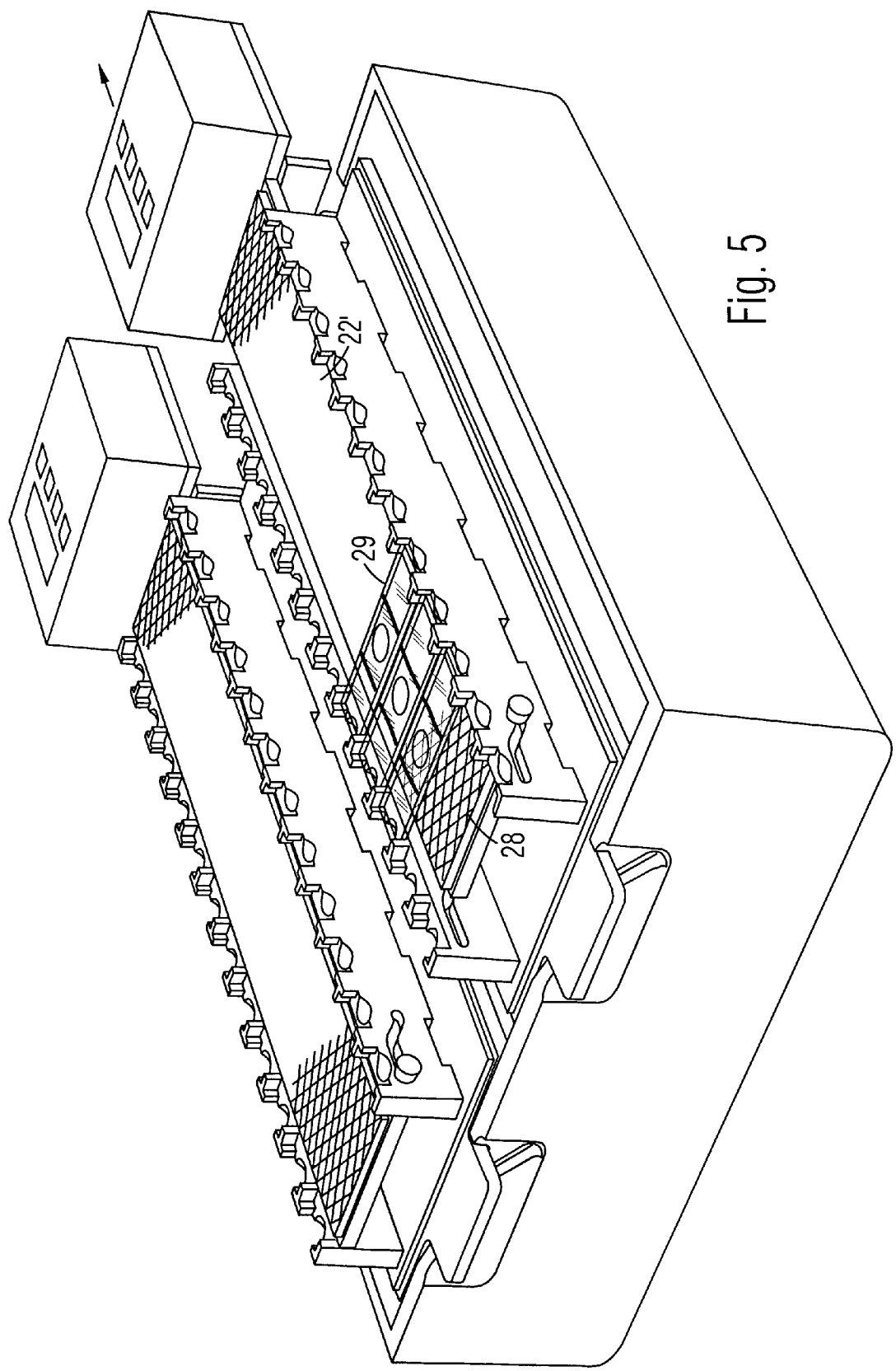
FIG. 5 is a side perspective view of the microscope slide stainer with the hot bar on one of the slide supporting racks in a lowered position.

FIG. 5:

After slides 29 are heated long enough, heating can be stopped immediately by moving hot plate 22' in the direction indicated by the arrow in FIG. 5 to the lowered position to disengage it from slides 29. Grooves 28 enable hot plate 22' to be easily separated from wet slides 29 by providing air channels under the slides and preventing suction. Hot plate 22' can be moved back to the raised position to quickly begin heating again if desired.

Figure 6:
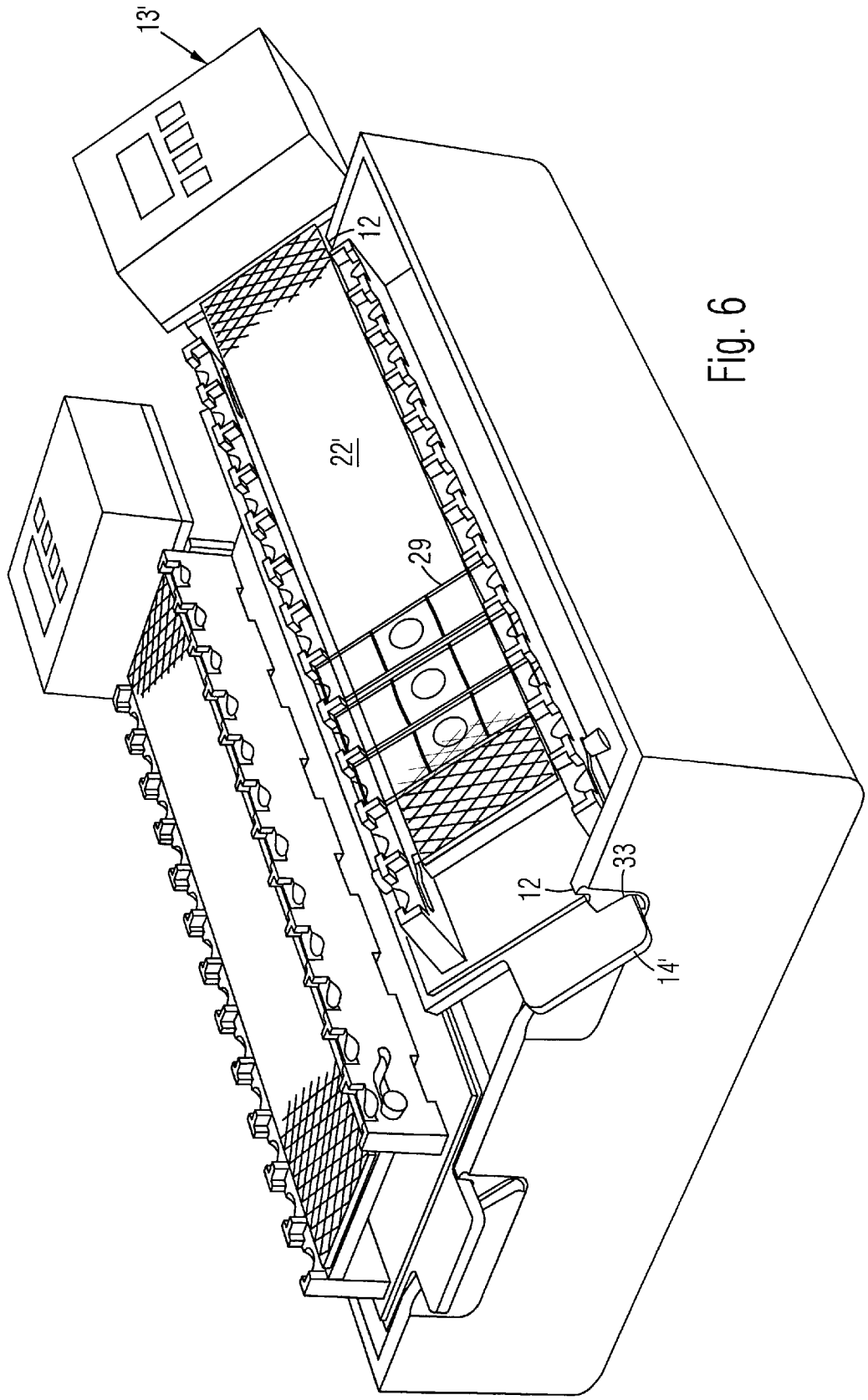
FIG. 6 is a side perspective view of the microscope slide stainer with one of the slide supporting racks in a tilted position.

FIG. 6:

In FIG. 6, slide supporting rack 13' is placed in a tilted position for rinsing off the reagent by inserting tabs 14' (one shown) in slanted supporting slots 33 (one shown) extending downwardly from notches 12 on bin 10. Because slides 29 are spaced laterally from each other, and also spaced above lowered hot plate 22', the rinsing fluid will drain into the gaps between slides 29 without crossing over onto adjacent slides. Slides 29 are not touched by hand during heating or rinsing. Therefore, cross contamination between slides is eliminated. The rinsing fluid and reagent are collected in bin 10.

SUMMARY AND SCOPE

Accordingly, a microscope slide stainer is provided. It stains microscope slides. It reduces human handling of the slides by holding the slides during heating and rinsing. It heats the slides to selectable temperatures with a controllable hot plate. It starts and stops the heating very quickly by mechanically engaging and disengaging the hot plate from the slides. It enables the slides to be seen clearly against a white colored hot plate. It prevents radiated heat loss for faster warm up. It prevents the slides from drying out. It prevents the wet slides from sticking to the hot plate during disengagement. It tilts the slides to assist runoff during rinsing. It prevents the runoff from each slide from crossing over onto adjacent slides so as to eliminate cross contamination. It is particularly suitable for applications such as special stains, immunohistochemistry (including frozen sections, paraffin-embedded tissues, cell culture, and culture cells on coverslips), and in situ hybridization techniques (including DNA, mRNA, and Peptide Nucleic Acid).

Although the above description is specific, it should not be considered as a limitation on the scope of the invention, but only as an example of the preferred embodiment. Many variations are is possible within the teachings of the invention. For example, grooves 28 can be arranged in other patterns. Brackets 19 can be of other shapes. Direction-changing slots 26 and 27 can be of other shapes, such as two horizontal sections connected by a vertical section. Cover 32 can be transparent for enabling slide viewing during heating, but at the cost of reduced insulation. Grooves 27 can also extend through rails 15, and pins 25 can also be thumb-screw pins. Pins 24 and 25 can also be non-removable. More or fewer pairs of notches can be provided on bin 10 for supporting more or fewer racks 13. Therefore, the scope of the invention should be determined by the appended claims and their legal equivalents, not by the examples given.

We claim:

1. A microscope slide heater, comprising:

an elongated slide supporting rack with a pair of spaced apart parallel rails for holding a plurality of microscope slides transversely there between;

a plurality of brackets arranged on top of said rails defining a plurality of spaced-apart slide holding positions for holding said slides in spaced apart positions, wherein said brackets on one of said rails are disconnected from said brackets on the other one of said rails to provide air gaps between said slides for preventing a rinsing fluid from crossing over adjacent ones of said slides; and an elongated hot plate positioned between said rails and movable to a raised position for engaging bottoms of said slides and heating said slides, said hot plate being also movable to a lowered position for disengaging from said slides to instantly stop heating said slides, and for allowing said rinsing fluid to run off between said slides without crossing over adjacent ones of said slides.

2. The microscope slide heater of claim 1, further including a plurality of drainage slots arranged at a lower end of one of said rails for draining said rinsing fluid.

3. The microscope slide heater of claim 1, further including a cover removably positioned on top of and sealed against said rack to define a heating and humidity chamber for preventing said slides from drying out, said cover being opaque for preventing radiant heat loss and reducing warm up time.

4. A microscope slide heater, comprising:

an elongated slide supporting rack with a pair of spaced apart parallel rails for holding a plurality of microscope slides transversely there between;

a plurality of brackets arranged on top of said rails defining a plurality of spaced-apart slide holding positions for holding said slides in spaced apart positions, wherein said brackets on one of said rails are disconnected from said brackets on the other one of said rails to provide air gaps between said slides for preventing a rinsing fluid from crossing over adjacent ones of said slides;

an elongated hot plate positioned between said rails and movable to a raised position for engaging bottoms of said slides and heating said slides, said hot plate being also movable to a lowered position for disengaging from said slides to instantly stop heating said slides, and for allowing said rinsing fluid to run off between said slides without crossing over adjacent ones of said slides; and a plurality of grooves arranged on a top surface of said hot plate to provide a plurality of air channels arranged for being positioned under each of said slides for preventing said slides, when wet, from sticking to said hot plate, and when said hot plate is in said raised position, said grooves are also for providing drainage between said slides for preventing said rinsing fluid from flowing onto adjacent ones of said slides.

5. The microscope slide heater of claim 1, wherein said grooves are arranged in a diamond-shaped pattern.

6. A microscope slide heater, comprising:

A microscope slide heater, comprising:

an elongated slide supporting rack with a pair of spaced apart parallel rails for holding a plurality of microscope slides transversely there between;

an elongated hot plate positioned between said rails and movable to a raised position for engaging bottoms of said slides and heating said slides, said hot plate being also movable to a lowered position for disengaging from said slides to instantly stop heating said slides, and for allowing a rinsing fluid to run off between said slides without crossing over adjacent ones of said slides; and a plurality of pins extending from opposite longitudinal edges of said hot plate, said pins being respectively positioned in a plurality of direction-changing slots in said rails, said slots each comprising an upper horizontal section and a lower horizontal section connected by a slanted section, said hot plate being guided by said slots to move between said raised position and said lowered position.

7. A microscope slide heater, comprising:

an elongated slide supporting rack with a pair of spaced apart parallel rails for holding a plurality of microscope slides transversely there between;

an elongated hot plate positioned between said rails and movable to a raised position for engaging bottoms of said slides and heating said slides, said hot plate being also movable to a lowered position for disengaging from said slides to instantly stop heating said slides, and for allowing a rinsing fluid to run off between said slides without crossing over adjacent ones of said slides; and a pair of tabs generally at opposite ends of said rack, and a waste collection bin with an open top, said rack being supported in a horizontal position for heating said slides when said tabs are positioned horizontally on opposite rims of said bin, said bin including a pair of slanted supporting slots extending downwardly into said opposite rims thereof, said rack being positioned in a tilted position for rinsing said slides when said tabs are inserted into said slanted supporting slots.

8. A microscope slide heater, comprising:

an elongated slide supporting rack with a pair of spaced apart parallel rails for holding a plurality of microscope slides transversely there between;

an elongated hot plate positioned between said rails and movable to a raised position for engaging bottoms of said slides and heating said slides, said hot plate being also movable to a lowered position for disengaging from said slides to instantly stop heating said slides, and for allowing a rinsing fluid to run off between said slides without crossing over adjacent ones of said slides; and a heating element embedded within said hot plate, said heating element being arranged in a zigzag pattern which is denser at opposite ends of said hot plate to provide even heating across an entire length of said hot plate.

9. A microscope slide heater, comprising:

a waste collection bin with an open top, opposite rims, and a pair of slanted supporting slots extending downwardly into said opposite rims;

an elongated slide supporting rack supported in a horizontal position across said open top of said bin when opposite ends of said rack are positioned horizontally on said opposite rims, said rack including a pair of spaced apart parallel rails for holding a plurality of microscope slides transversely there between, said rack being positioned in a tilted position for rinsing said slides when said opposite ends thereof are positioned in said slanted supporting slots on said bin; and an elongated hot plate movably positioned between said rails of said rack, a plurality of pins extending from opposite longitudinal edges of said hot plate, said pins being respectively positioned in a plurality of direction-changing slots in said rails, said slots each comprising an upper horizontal section and a lower horizontal section connected by a slanted section, said hot plate being movable to a raised position for engaging bottoms of said slides and heating said slides, said hot plate being also movable to a lowered position for disengaging from said slides to instantly stop heating said slides, and for allowing a rinsing fluid to run off between said slides without crossing over adjacent ones of said slides, said hot plate including a plurality of grooves arranged on a top surface thereof to provide a plurality of air channels for preventing said slides, when wet, from sticking to said hot plate, and when said hot plate is in said raised position, said grooves are also for providing drainage for preventing said rinsing fluid from flowing across adjacent ones of said slides.

10. The microscope slide heater of claim 9, wherein said grooves on said hot plate are arranged in a diamond-shaped pattern for efficient drainage.

11. The microscope slide heater of claim 9, further including a plurality of brackets arranged on top of said rails defining a plurality of spaced-apart slide holding positions for holding said slides in spaced apart positions for preventing said rinsing fluid from crossing over adjacent ones of said slides.

12. The microscope slide heater of claim 9, further including a heat resistant powder-coat paint on said hot plate.

13. The microscope slide heater of claim 9, further including a white color on top of said hot plate, said white color providing a light homogeneous background for facilitating viewing stained tissues on said slides.

14. The microscope slide heater of claim 9, further including a plurality of drainage slots arranged at a lower end of one of said rails for draining said rinsing fluid.

15. The microscope slide heater of claim 9, further including a control box connected to said hot plate for temperature control.

16. The microscope slide heater of claim 9, further including a heating element embedded within hot plate, said heating element being arranged in a zigzag pattern which is denser at opposite ends of said hot plate to provide even heating across an entire length of said hot plate.

17. The microscope slide heater of claim 9, further including a cover removably positioned on top of said rack to define a heating and humidity chamber for preventing said slides from drying out, said cover being opaque for preventing radiant heat loss and reducing warm up time.

18. The microscope slide heater of claim 9, further including a cover removably positioned on top of said rack to define a heating and humidity chamber for preventing said slides from drying out, said cover being transparent for facilitating slide viewing.

19. A microscope slide heater, comprising:

a waste collection bin with an open top and opposite rims, a pair of supporting notches arranged on said opposite rims, and a pair of slanted supporting slots extending downwardly into said opposite rims;

an elongated slide supporting rack with a pair of tabs generally at opposite ends thereof, said rack being supported in a horizontal position across said open top of said bin when said tabs are positioned in said supporting notches of said bin, said rack further including a pair of spaced apart parallel rails extending along a base, a plurality of drainage slots arranged at a lower end of one of said rails, a plurality of brackets arranged on top of said rails defining a plurality of spaced-apart slide holding positions for holding microscope slides in spaced apart positions for preventing a rinsing fluid from crossing over adjacent ones of said slides, said rack being positioned in a tilted position for rinsing said slides when said tabs are inserted in said slanted supporting slots on said bin; and an elongated hot plate movably positioned between said rails of said rack and spaced above said base of said rack, a plurality of pins extending from opposite longitudinal edges of said hot plate, said pins being respectively positioned in a plurality of direction-changing slots in said rails, said slots each comprising an upper horizontal section and a lower horizontal section connected by a slanted section, said hot plate being movable to a raised position for engaging bottoms of said slides and heating said slides, and also movable to a lowered position for disengaging from said slides and instantly stop heating said slides, said hot plate including a plurality of grooves arranged on a top surface thereof to provide a plurality of air channels for preventing said slides, when wet, from sticking to said hot plate, and when said hot plate is in said raised position, said grooves are also for providing drainage for preventing said rinsing fluid from flowing across adjacent ones of said slides.

20. The microscope slide heater of claim 19, wherein said grooves on said hot plate is arranged in a diamond-shaped pattern for efficient drainage.

21. The microscope slide heater of claim 19, further including a control box connected to said hot plate for precise temperature control.

22. The microscope slide heater of claim 19, further including a heating element embedded within hot plate, said heating element is arranged in a zigzag pattern which is denser at opposite ends of said hot plate for providing even heating across an entire length of said hot plate.

23. The microscope slide heater of claim 19, further including a heat resistant powder-coat paint on said hot plate.

24. The microscope slide heater of claim 19, further including a white color on top of said hot plate, said white color providing a light homogeneous background for facilitating viewing stained tissues on said slides.

25. The microscope slide heater of claim 19, further including a cover removably positioned on top of said rack to define a heating and humidity chamber for preventing said slides from drying out, said cover being opaque for preventing radiant heat loss and reducing warm up time.

26. The microscope slide heater of claim 19, further including a cover removably positioned on top of said rack to define a heating and humidity chamber for preventing said slides from drying out, said cover being transparent for facilitating slide viewing.

* * * * *